(12) United States Patent
Choi et al.

(10) Patent No.: US 12,371,720 B2
(45) Date of Patent: *Jul. 29, 2025

(54) METHOD FOR PREPARING BLOCK COPOLYMER

(71) Applicant: LG CHEM, LTD., Seoul (KR)

(72) Inventors: Jung Yun Choi, Daejeon (KR); Chul Woong Kim, Daejeon (KR); Sungwoon Heo, Daejeon (KR); Donggyun Kang, Daejeon (KR); Jae Hyung Kim, Daejeon (KR); Suhyun Cho, Daejeon (KR)

(73) Assignee: LG CHEM, LTD., Seoul (KR)

( * ) Notice: Subject to any disclaimer, the term of this patent is extended or adjusted under 35 U.S.C. 154(b) by 639 days.

This patent is subject to a terminal disclaimer.

(21) Appl. No.: 17/629,485

(22) PCT Filed: Sep. 11, 2020

(86) PCT No.: PCT/KR2020/012318
§ 371 (c)(1),
(2) Date: Jan. 24, 2022

(87) PCT Pub. No.: WO2021/049910
PCT Pub. Date: Mar. 18, 2021

(65) Prior Publication Data
US 2022/0267815 A1   Aug. 25, 2022

(30) Foreign Application Priority Data

Sep. 11, 2019  (KR) .................. 10-2019-0113112

(51) Int. Cl.
| C12P 7/625 | (2022.01) |
| C08G 63/08 | (2006.01) |
| C08G 81/02 | (2006.01) |
| C12N 9/10  | (2006.01) |

(52) U.S. Cl.
CPC .............. *C12P 7/625* (2013.01); *C08G 63/08* (2013.01); *C08G 81/027* (2013.01); *C12N 9/1029* (2013.01); *C12N 9/13* (2013.01); *C12Y 208/03001* (2013.01)

(58) Field of Classification Search
None
See application file for complete search history.

(56) References Cited

U.S. PATENT DOCUMENTS

| 6,472,188 B1 | 10/2002 | Lee et al. |
| 2011/0046339 A1 | 2/2011 | Park et al. |
| 2011/0177569 A1 | 7/2011 | Park et al. |
| 2011/0245420 A1 | 10/2011 | Rasal et al. |
| 2014/0018574 A1 | 1/2014 | Raith et al. |
| 2015/0018497 A1 | 1/2015 | Farrugia et al. |
| 2020/0172680 A1 | 6/2020 | Choi et al. |
| 2020/0270649 A1* | 8/2020 | Kang ................. C08G 63/06 |
| 2021/0309800 A1* | 10/2021 | Choi ................. C08G 63/08 |

FOREIGN PATENT DOCUMENTS

| CN | 1908030 | 2/2007 | |
| CN | 107522852 | 12/2017 | |
| CN | 107602834 | 1/2018 | |
| JP | H2-84431 A | 3/1990 | |
| JP | H06-298921 | 10/1994 | |
| JP | H07-316271 | 12/1995 | |
| JP | 2010-510372 | 4/2010 | |
| JP | 2015-17251 | 1/2015 | |
| KR | 10-0250830 | 4/2000 | |
| KR | 10-2008-0046795 | 5/2008 | |
| KR | 20080046795 A * | 5/2008 | ............. C08G 63/88 |
| KR | 10-0957773 | 5/2010 | |
| KR | 10-2015-0032579 | 3/2015 | |
| KR | 10-2017-0028186 | 3/2017 | |
| KR | 10-2018-0072481 | 6/2018 | |
| KR | 10-2019-0060584 | 6/2019 | |
| KR | 10-2019-0083816 | 7/2019 | |
| KR | 10-2019-0108892 | 9/2019 | |
| WO | 2009-022797 | 2/2009 | |
| WO | 2019-0135582 A1 | 7/2019 | |
| WO | WO-2019177371 A1 * | 9/2019 | ............. C08G 63/06 |

OTHER PUBLICATIONS

Don et al., Studies on the alcoholysis of poly(3-hydroxybutyrate) and the synthesis of PHB-b-PLA block copolymer for the preparation of PLA/PHB-b-PLA blends, J. Polymer Res 25, 2018: 38. (Year: 2018).*
Meng et al., Production and characterization of poly(3-hydroxypropionate-co-4-hydroxybutyrate) with fully controllable structures by recombinant *Escherichia coli* containing an engineered pathway, Metabolic Eng. 14, 2012, 317-24. (Year: 2012).*
Jacobsen et al., Polylactide, Polymer Eng. Sci. 39, 1999, 1311-19. (Year: 1999).*
Yalpani et al., Syntheses of Poly(3-hydroxyalkanoate) (PHA) Conjugates: PHA-Carbohydrate and PHA-Synthetic Polymer Conjugates, Macromolecules 24, 1991, 6046-49. (Year: 1991).*
Gumel et al., Chapter 7: Modification of Polyhydroxyalkanoates (PHAs), RSC Green Chemistry No. 30 (Roy, ed.), 2015). (Year: 2015).*
U.S. Appl. No. 17/269,963.
Ramier et al., " Microwave-Assisted Synthesis and Characterization of Biodegradable Block Copolyesters Based on Poly(3-hydroxyalkanoate)s and Poly($_{D,L}$-lactide)," J. Polym. Sci. Part A: Polym. Chem. 50(7):1445-1455 (2012).

(Continued)

Primary Examiner — Todd M Epstein
(74) Attorney, Agent, or Firm — Bryan Cave Leighton Paisner LLP

(57) ABSTRACT

Provided is a method for preparing a block copolymer including a step of subjecting a lactide monomer to ring-opening polymerization in the presence of a biosynthesized poly(3-hydroxypropionate) initiator to prepare a polylactide-poly(3-hydroxypropionate) block copolymer.

10 Claims, 1 Drawing Sheet

(56) References Cited

OTHER PUBLICATIONS

Tripathi et al., "Biosynthesis and Characterization of Diblock Copolymer of P(3-Hydroxypropionate)-block-P(4-hydroxybutyrate) from Recombinant *Escherichia coli*," Biomacromolecules 14(3):862-870 (2013).

Lee, "Control of Molecular Weight and Terminal Groups of Poly(3-hydroxybutyrate) in Bio-synthesis," Textile Coloration and Finishing, The Korean Society of Dyers and Finishers, 30(2):130-140 (2018). English Machine Translation included.

Lebarbé et al., "Fully bio-based poly($_L$-lactide)-b-poly(ricinoleic acid)-b-poly($_L$-lactide) triblock copolyesters: investigation of solid-state morphology and thermos-mechanical properties," Polymer Chemistry 4:3357-3369 (2013).

Ren et al., "Microbial synthesis of a novel terpolyester P(LA-co-3HB-co-3HP) from low-cost substrates," Microb. Biotechnol. 10(2):371-380 (2017).

Supthanyakul et al., "Poly(l-lactide-b-butylene succinate-b-l-lactide) triblock copolymer: A multi-functional additive for PLA/PBS blend with a key performance on film clarity," Polymer Degradation and Stability (2017), 142:160-168.

Çatiker et al., "Synthesis and characterization of novel ABA type poly(Ester-ether) triblock copolymers," Journal of Polymer Research 26(5): 123, p. 1-9 (2019).

Williams et al., "Applications of PHAs in Medicine and Pharmacy," in Biopolymers Online, A. Steinbüchel (ed.), pp. 91-103, (2005), doi: 10.1002/3527600035.bpol4004.

Zhao et al., "Biosynthesis of Poly (3-hydroxypropionate-co-lactate) from Glycerol by Engineered *Escherichia coli*," China Biotechnology 38(2):46-53 (2018). English Language Abstract included.

Hiki et al., "Synthesis and characterization of hydroxyl-terminated [RS]-poly(3-hydroxybutyrate) and its utilization to block copolymerization with $_L$-lactide to obtain a biodegradable thermoplastic elastomer," Polymer 41:7369-7379 (2000).

Lee et al., "Microbial production of building block chemicals and polymers," Current Opinion in Biotechnology 22:758-767 (2011).

Wu et al., "Synthesis, characterization and biocompatibility of novel biodegradable poly[((R)-3-hydroxybutyrate)-block-(D,L-lactide)-block-(ε-caprolactone)] triblock copolymers," Polymer International 57(7):939-949 (2008).

Haynes et al., "In Situ Copolyesters Containing Poly($_L$-lactide) and Poly(hydroxyalkanoate) Units," Biomacromolecules 8(4):1131-1137 (2007).

Pholharn et al., "Ring opening polymerization of poly(L-lactide) by macroinitiator," AIP Conference Proceedings 2065 (1):030016 (2019), 6 pages, doi.org/10.1063/1.5088274.

Zhang et al., "A New Synthetic Route to Poly[3-hydroxypropionic acid] (P[3-HP]): Ring-Opening Polymerization of 3-HP Macrocyclic Esters," Macromolecules 37(22):8198-8200 (2004).

* cited by examiner

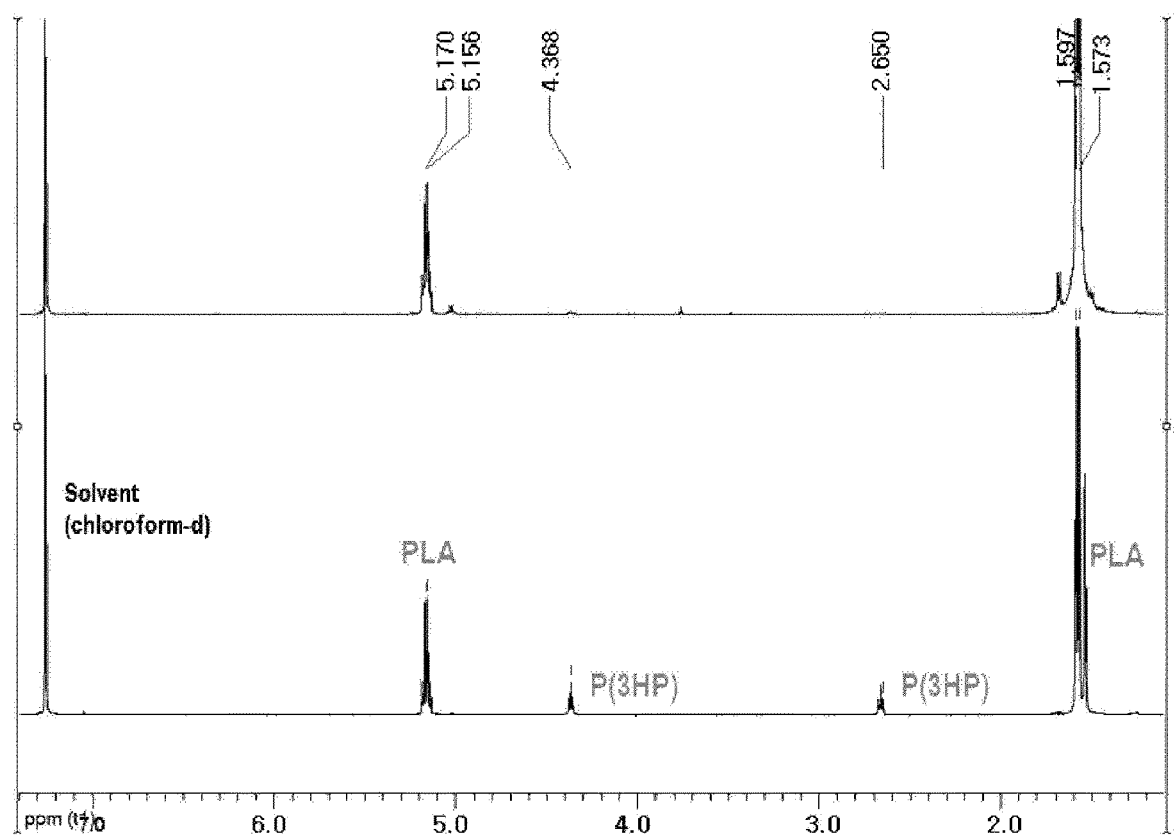

METHOD FOR PREPARING BLOCK COPOLYMER

CROSS-REFERENCE TO RELATED APPLICATION(S)

This application is a National Stage Application of International Application No. PCT/KR2020/012318 filed on Sep. 11, 2020, which claims the benefit of Korean Patent Application No. 10-2019-0113112 filed on Sep. 11, 2019 with the Korean Intellectual Property Office, the disclosure of which is incorporated herein by reference in its entirety.

TECHNICAL FIELD

The present disclosure relates to a method for preparing a polylactide-poly(3-hydroxypropionate) block copolymer, and more particularly to a method for preparing a polylactide-poly(3-hydroxypropionate) block copolymer using biosynthesized poly(3-hydroxypropionate) as an initiator.

BACKGROUND

Polylactide (or polylactic acid) resin is a plant-derived resin obtained from plants such as corn, and is attracting attention as an environment-friendly material having excellent tensile strength and elastic modulus while having biodegradable properties. Specifically, unlike petroleum-based resins such as polystyrene resin, polyvinyl chloride (PVC) resin, polyethylene and the like that have been used in the past, since the polylactide resin has the effects of preventing the depletion of petroleum resources and suppressing the emission of carbon dioxide, it can reduce environmental pollution, which is a drawback of petroleum-based plastic products. Therefore, as the problem of environmental pollution caused by waste plastic, etc. emerges as a social problem, it is striving to enlarge the range of application to the fields of products using general plastics (petroleum-based resins), such as food packaging materials and containers, and electronic product cases.

However, the polylactide resin has lower impact resistance and heat resistance than the conventional petroleum-based resin, and thus its applicable range is limited. In addition, it has poor elongation at break properties and easily exhibits brittleness, which has limitations as a general-purpose resin.

Therefore, in the existing technology, research is underway to improve physical properties through the process of compounding materials such as PBS (poly(butylene succinate)) and PBAT (poly(butylene adipate-co-terephthalate)), which are biodegradable and have relatively excellent elongation properties, together with polylactide, or through the formation of a block copolymer. However, in the case of PBS and PBAT, there is a problem that the tensile strength is low, and thus, the tensile strength of the compound or block copolymer is also lowered.

In addition, poly(3-hydroxypropionate), which is a biodegradable polymer, has a low glass transition temperature (Tg) of $-20°$ C. while having excellent mechanical properties, and has high elongation, so when combined with polylactic acid, it has the advantage that both biodegradability and mechanical properties can be excellently maintained. However, there is a limit to increasing the molecular weight of poly(3-hydroxypropionate) through a chemical synthesis method.

BRIEF DESCRIPTION

Technical Problem

It is an object of the present disclosure to provide a polylactide-poly(3-hydroxypropionate) block copolymer having excellent mechanical properties such as tensile modulus, tensile strength, elongation at break and impact strength while maintaining environmental affinity and biodegradability, by using, as an initiator, poly(3-hydroxypropionate), which is prepared through biosynthesis and is easily increased in the molecular weight.

Technical Solution

While the present disclosure is susceptible to various modifications, exemplary embodiments thereof have been shown by way of specific examples in the drawings and are herein described in detail. It should be understood, however, that the description herein of specific embodiments is not intended to limit the invention, but on the contrary, the intention is to cover all modifications, equivalents, and alternatives falling within the spirit and scope of the invention. In the description of the present disclosure, when a detailed description of well-known technology relating to the present disclosure can unnecessarily make unclear the spirit of the present disclosure, a detailed description thereof will be omitted.

The present disclosure provides a method for preparing a block copolymer including the step of subjecting a lactide monomer to a ring-opening polymerization in the presence of a biosynthetically prepared poly(3-hydroxypropionate) initiator to prepare polylactide-poly (3-hydroxypropionate) block copolymer. Preferably, the method for preparing a block copolymer according to the present disclosure comprises the following steps:

(a) biosynthesizing a poly(3-hydroxypropionate) initiator; and (b) subjecting a lactide monomer to a ring-opening polymerization in the presence of the poly(3-hydroxypropionate) initiator prepared in step (a) to prepare a polylactide-poly(3-hydroxypropionate) block copolymer.

Additionally, the method for preparing a block copolymer according to the present disclosure can further include, between steps (a) and (b), a step of subjecting the poly (3-hydroxypropionate) initiator biosynthesized in step (a) to hydrolysis or the like to adjust the molecular weight.

Advantageous Effects

According to the present disclosure, as poly(3-hydroxypropionate) produced by biosynthesis rather than chemical synthesis is appropriately treated as needed to have various molecular weights and is used as an initiator, it can be applied to various fields by utilizing the physical properties of the polylactide-poly(3-hydroxypropionate) block copolymer that varies depending on the structure and molecular weight. In addition, a polylactide-poly(3-hydroxypropionate) block copolymer having excellent mechanical properties such as tensile modulus, tensile strength, elongation at break and impact strength, while maintaining environmental affinity and biodegradability can be provided.

BRIEF DESCRIPTION OF THE DRAWINGS

FIG. 1 is a graph showing the results of NMR analysis of the block copolymer prepared in Example 1-4.

DETAILED DESCRIPTION

Hereinafter, a method for preparing a block copolymer according to a specific embodiment of the present disclosure will be described in more detail.

Unless specifically indicated herein, the term "including" or "containing" refers to including some element (or component) without any limitation, and should not be construed as excluding addition of other elements (or components).

Also, in the entire specification, the term "lactide monomer" can be defined as follows. Typically, lactides can be classified into L-lactide consisting of L-lactic acid, D-lactide consisting of D-lactic acid, and meso-lactide consisting of an L-type and a D-type. Also, a mixture of L-lactide and D-lactide in a weight ratio of 50:50 is referred to as D,L-lactide or rac-lactide. Among these lactides, the polymerization proceeding only with either of L-lactide and D-lactide that have a high level of optical purity is known to yield an L- or D-polylactide (PLLA or PDLA) with a high level of stereoregularity. Such polylactides have a faster crystallization rate and a higher crystallization degree than a polylactide having a low level of optical purity. However, the term 'lactide monomer' is defined to include all types of lactides regardless of the characteristic differences of lactides depending on their types and the characteristic differences of the polylactides as obtained therefrom.

And, in the entire specification, the term "polylactide-poly(3-hydroxypropionate) block copolymer" refers to polylactide-poly(3-hydroxypropionate) block copolymer including polylactide repeating units and poly(3-hydroxypropionate) repeating units. The "polylactide-poly(3-hydroxypropionate) block copolymer" can be prepared by a process including the step of subjecting "lactide monomer" to a ring-opening polymerization in the presence of the above-mentioned poly(3-hydroxypropionate) initiator to form the polylactide repeating unit and the poly(3-hydroxypropionate) repeating unit. The polymer obtained after the completion of such ring-opening polymerization and the formation of the repeating unit can be referred to as the "polylactide-poly(3-hydroxypropionate) block copolymer". As mentioned above, the category of the 'lactide monomer' includes any types of lactides.

In the category of the polymer that can be referred to as the "polylactide-poly(3-hydroxypropionate) block copolymer", all the polymers are included in any state after the completion of the ring-opening polymerization and the formation of the repeating unit, for example, unpurified or purified polymers after the completion of the ring-opening polymerization, the polymers contained in the liquid or solid resin composition prior to being molded into an article, or the polymers contained in plastics or woven materials after being molded into an article. Accordingly, in the entire specification, properties of the "polylactide-poly(3-hydroxypropionate) block copolymer" (such as weight average molecular weight) can be defined by the properties of the polymer in any state after the completion of the ring-opening polymerization and the formation of the repeating unit.

Meanwhile, the present inventors have found that when poly(3-hydroxypropionate) is synthesized by biosynthesis and used, block copolymers having various physical properties can be prepared by increasing the molecular weight of poly(3-hydroxypropionate) which acts as an initiator in the preparation of polylactide-poly(3-hydroxypropionate) block copolymer, or by adjusting the molecular weight in various ways such as adjusting the molecular weight through hydrolysis, thereby completing the present disclosure.

According to one embodiment of the invention, a block copolymer can be prepared by a process including the step of subjecting a lactide monomer to a ring-opening polymerization in the presence of the poly(3-hydroxypropionate) prepared by biosynthesis, to prepare a polylactide-poly(3-hydroxypropionate) block copolymer.

In general, the polymerization reaction of a polylactide resin by ring-opening polymerization of lactide monomers is initiated by a compound having a terminal hydroxy group, and lactide monomers are continuously ring-opened and inserted into the compound having a terminal hydroxy group.

Therefore, the poly(3-hydroxypropionate) initiator includes a hydroxy group and/or an alkoxy group at the terminal, and when the hydroxy group and/or the alkoxy group, which is the terminal end of the poly(3-hydroxypropionate) initiator, is added to the ring-opening polymerization reaction of lactide monomers, the lactide monomer starts to be added at the end, and consequently the polylactide-poly(3-hydroxypropionate) block copolymer is prepared.

Therefore, when the ring-opening polymerization reaction of the lactide monomer is performed in the presence of the poly(3-hydroxypropionate) initiator, the poly(3-hydroxypropionate) functions as a polymerization initiator and is also included as a repeating unit in the block copolymer, thereby improving flexibility and mechanical properties such as impact strength of the finally prepared block copolymer. Specifically, because the poly (3-hydroxypropionate) is included in the finally prepared block copolymer, the glass transition temperature (Tg) of the block copolymer can be lowered and so the flexibility can be increased.

The present disclosure is characterized in that poly(3-hydroxypropionate) used as such an initiator is produced by biosynthesis.

The term "biosynthesis" as used herein refers to the synthesis and preparation of a substance of interest using an organism rather than chemical synthesis, and the organism is preferably a microorganism, and such a microorganism can be a recombinant microorganism.

The biosynthesis can be used without limitation as long as it is a biosynthetic method capable of synthesizing poly(3-hydroxypropionate), and a method known in the art as a biosynthesis method of poly(3-hydroxypropionate) can also be used. For example, the poly(3-hydroxypropionate) can be prepared by fermenting an appropriate substrate using microorganisms capable of synthesizing poly(3-hydroxypropionate) in an appropriate medium. As the substrate, purified and unpurified substrates can be used without limitation. In order to prepare polyhydroxyalkanoate (PHA) such as poly(3-hydroxypropionate) in microorganisms, enzymes that convert microbial metabolites into PHA monomers and PHA synthase that synthesizes PHA polymers using PHA monomers are essential. PHA synthase synthesizes PHA using hydroxyacyl-CoA as a substrate, and as an enzyme capable of providing hydroxyacyl-CoA, which is a substrate for PHA, there have been known α-ketothiolase (PhaA) derived from *Ralstonia eutropha*, etc., acetoacetyl-CoA reductase (PhaB), 3-hydroxydecanoyl-ACP:CoA transferase: PhaG derived from *Pseudomonas*, (R)-specific enoyl-CoA hydratase: PhaJ derived from *Aeromonas caviae* and *Pseudomonas aeruginosa*, 3-ketoacyl-ACP reductase (FabG) derived from *E. coli* and *Pseudomonas aeruginosa*, etc. These microorganisms are microorganisms that contain an enzyme capable of providing hydroxyacyl-CoA and/or a polyhydroxyalkanoate synthase gene, and can be a microorganism that originally has these genes or can be a microorganism obtained by transforming the genes by recombination. For example, various microorganisms are known as microbial cells that originally have the PHA synthase gene (Korean Patent Registration No. 10-250830). It is also good to transform microorganisms such as *E. coli*. Microorganisms that can be transformed with a recombinant vector include both prokaryotic and eukaryotic cells, and a host having a high DNA introduction efficiency and a high expression efficiency of the introduced DNA can usually be used. Specific examples can include well-known eukaryotic and prokaryotic hosts, such as *Escherichia* sp., *Pseudomonas* sp., *Bacillus* sp., *Streptomyces* sp., *Erwinia* sp., *Serratia* sp., *Providencia* sp., *Corynebacterium* sp., *Leptospira* sp., *Salmonella* sp., *Brevibacterium* sp., *Hyphomonas* sp., *Chromobacterium* sp., *Nocardia* sp. fungi or yeast, including *E. coli* (e.g., *E. coli* DH5a, *E. coli* JM101, *E. coli* K12, *E. coli* W3110, *E. coli* X1776, *E. coli* B and *E. coli* XL1-Blue), without being limited thereto. When transformed into a suitable host, the vector can replicate and function independently of the host genome, or in some cases can be integrated into the genome itself.

Further, in addition to the substrate, glucose, fructose, sucrose, dextrose, triglyceride, fatty acid, etc. can be further included in the medium, and as the medium, a known medium can be selected and used without limitation as long as it contains only a carbon source for fermentation of the microorganisms. Examples thereof include MR medium, M9 medium, LB medium, or the like.

Examples of the biosynthesis method of poly(3-hydroxypropionate) include, but are not limited to, those disclosed in Korean Patent Publication No. 10-2019-0060584, and the use of poly(3-hydroxypropionate) synthesized by a method capable of biosynthesizing poly(3-hydroxypropionate) by any route is included within the scope of the present disclosure.

When using poly(3-hydroxypropionate) by biosynthesis in this way, unlike chemical synthesis, poly(3-hydroxypropionate) having various molecular weights can be obtained. For example, in the present disclosure, poly(3-hydroxypropionate) having high molecular weight can also be synthesized by biosynthesis and used as a macroinitiator, and poly(3-hydroxypropionate) whose molecular weight is reduced through hydrolysis can also be used. The hydrolyzing agent can be used without limitation as long as it is a hydrolyzing agent that can be used for hydrolysis of poly (3-hydroxypropionate), but for example, a known acid or base hydrolyzing agent, or PHA depolymerase, or a combination thereof can be used. One exemplary basic hydrolyzing agent is an alkali metal hydroxide, such as sodium hydroxide (e.g., an aqueous solution of sodium hydroxide), and one exemplary acidic hydrolyzing agent can be hydrochloric acid. Further, the hydrolyzing agent can be water alone in a heated state (e.g., from a temperature higher than room temperature to boiling point), or a dilute acid in a slightly heated state (e.g., from a temperature higher than room temperature to about 80° C.). Hydrolysis can be performed, for example, by a process in which the poly(3-hydroxypropionate) to be hydrolyzed is mixed with a solution of a hydrolyzing agent dissolved in a solvent such as methanol, and then the mixture is heated for several hours 4 to 12 hours at room temperature to 200° C., preferably 40 to 150° C., more preferably 80 to 120° C., even more preferably at a temperature around 100° C., without being limited thereto. In the examples of the present disclosure, hydrolysis was performed at 100° C.

When a polylactide-poly(3-hydroxypropionate) block copolymer is prepared by subjecting a lactide monomer to a ring-opening polymerization in the presence of a poly(3-hydroxypropionate) initiator, the amount of the poly(3-hydroxypropionate) initiator can be determined within an appropriate range, considering the content of repeating units of poly(3-hydroxypropionate) contained in the finally prepared block copolymer and the molar ratio of the hydroxy group and/or the alkoxy group of the initiator required for initiation of the minimum polymerization. Optimizing the flexibility and mechanical properties of the final block copolymer and considering the minimal content required as the initiator of the ring-opening polymerization, the poly(3-hydroxypropionate) initiator can be added in an amount of 0.01 parts by weight or more, 0.1 parts by weight to 100 parts by weight, 0.5 to 90 parts by weight, 0.7 to 80 parts by weight, or 0.9 to 70 parts by weight, based on 100 parts by weight of the lactide monomer.

The poly(3-hydroxypropionate) initiator can have a weight average molecular weight of 1,500 to 200,000, 2,000 to 150,000, 4,000 to 120,000, 5000 to 900,000, or 7,000 to 30,000 in order to exhibit excellent physical properties of the block copolymer without deterioration of polymerization activity. As the molecular weight of poly (3-hydroxypropionate) is larger, the crystallinity is better and the physical properties of the prepared block copolymer is better. If the weight average molecular weight of the poly(3-hydroxypropionate) initiator is less than 1,500, the crystallinity of poly(3-hydroxypropionate) is lowered and the molecular weight of the prepared block copolymer is also lowered, and so it is difficult to exhibit excellent physical properties. If the weight average molecular weight of the poly(3-hydroxypropionate) initiator exceeds 200,000, the polymerization activity is reduced, the block copolymer may not be synthesized and it may appear in a blended form. In the present disclosure, poly(3-hydroxypropionate) can be synthesized by biosynthesis and, if necessary, subjected to hydrolysis or the like to be easily adjusted within the above molecular weight range.

The reaction product containing the poly(3-hydroxypropionate) initiator prepared by biosynthesis and the lactide monomer are dried and then, the dried poly(3-hydroxypropionate) initiator and lactide monomer can be subjected to a ring-opening polymerization to prepare the above-mentioned block copolymer.

As the catalyst used for the ring-opening polymerization, any catalyst can be used without limitation as long as it is generally used in the preparation of a polylactide resin by a ring-opening polymerization reaction of lactide monomers. For example, the ring-opening polymerization can be performed under one or more catalysts selected from the group consisting of an organic metal complex catalyst and an organic catalyst.

The organic metal complex catalyst can be used without limitation in its composition, as long as it is generally used in the preparation of polylactide resins by the ring-opening polymerization of lactide monomers. For example, the organic metal complex catalyst can be a catalyst of the following Chemical Formula 1:

$$MA^1_p A^2_{2-p} \qquad \text{<Chemical Formula 1>}$$

wherein in Chemical Formula 1, M is Al, Mg, Zn, Ca, Sn, Fe, Y, Sm, Lu, Ti or Zr, p is an integer of 0 to 2, and $A^1$ and $A^2$ are each independently an alkoxy or carboxyl group.

More specifically, the $MA^1_p A^2_{2-p}$ can be tin(II) 2-ethylhexanoate ($Sn(Oct)_2$, hereinafter, also referred to as tin octoate).

Meanwhile, the organic catalyst can be used without limitation in its composition, as long as it is generally used in the preparation of polylactide resins by the ring-opening polymerization of lactide monomers. For example, the organic catalyst can be one or more selected from the group consisting of the following 1,5,7-triazobicyclo-[4,4,0]dec-5-ene (TBD), the following 1,8-diazabicyclo[5.4.0]undec-7-ene (DBU), the following 7-methyl-1,5,7-triazabicyclo[4.4.0]dec-5-ene (MTBD), the following 4-dimethylaminopyridine (DMAP), 4-(1-pyrrolidinyl)pyridine (PPY), imidazole, triazolium, thiourea, tertiary amine and creatinine:

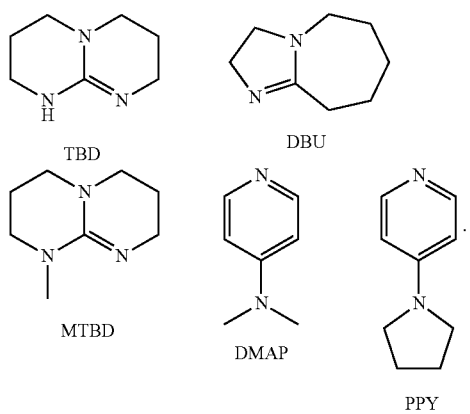

The imidazole can be one or more selected from the group consisting of the following compounds:

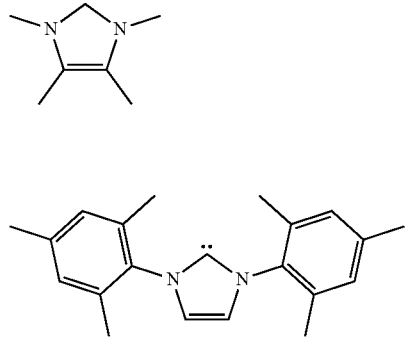

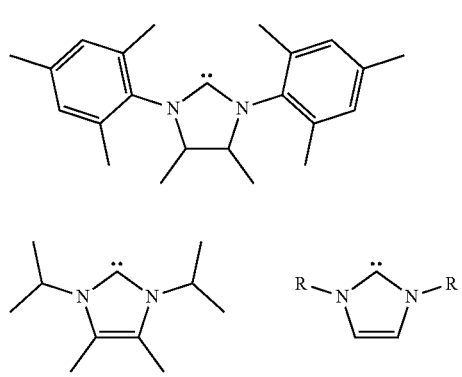

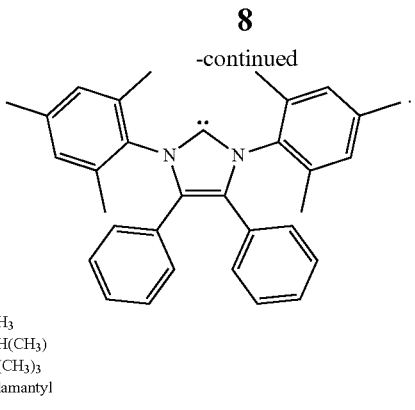

R = CH$_3$
R = CH(CH$_3$)
R = C(CH$_3$)$_3$
R = adamantyl

The triazolium can be the following compound:

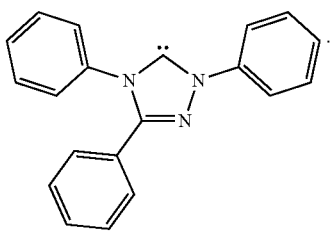

The thiourea can be one or more selected from the group consisting of the following compounds:

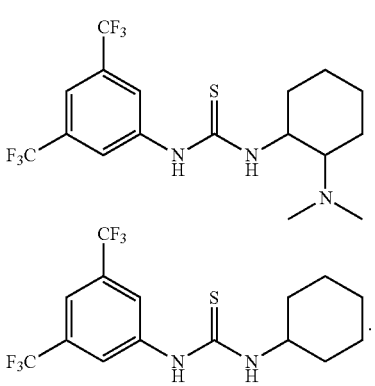

The tertiary amine can be one or more selected from the group consisting of the following compounds:

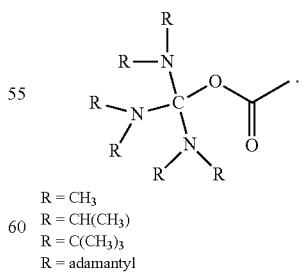

R = CH$_3$
R = CH(CH$_3$)
R = C(CH$_3$)$_3$
R = adamantyl

When the lactide ring-opening polymerization reaction is performed in the presence of the above-mentioned catalyst, depolymerization or decomposition of the finally prepared block copolymer can be suppressed, and a polylactide-poly (3-hydroxypropionate) block copolymer having a higher molecular weight and excellent mechanical properties can be obtained at a higher conversion rate.

In the method for preparing a block copolymer according to one embodiment, the content of the catalyst can be 0.01 to 10 mol %, 0.05 to 8 mol %, 0.07 to 5 mol %, or 0.09 to 3 mol % based on 100 mol % of the lactide monomer. If the content of the catalyst relative to 100 mol % of the lactide monomer is less than 0.01 mol %, the polymerization activity may not be sufficient, and if the content of the catalyst exceeds 10 mol %, the amount of residual catalyst of the prepared polylactide-poly(3-hydroxypropionate) block copolymer can increase, resulting in decomposition of the copolymer or reduction of molecular weight due to depolymerization such as transesterification reaction.

The ring-opening polymerization can be performed at 150 to 200° C. for 5 minutes to 10 hours.

In addition, the ring-opening polymerization reaction can be performed by bulk polymerization substantially using substantially no solvent. In this regard, using substantially no solvent can encompass use of a small amount of solvent for dissolving the catalyst, for example, at maximum of less than 1 ml of the solvent per 1 kg of the lactide monomer used. As the ring-opening polymerization is performed by bulk polymerization, a process of removing the solvent can be omitted after polymerization, and thus degradation or loss of the resin attributed to the solvent removal process can be prevented. Owing to the bulk polymerization, the polylactide-poly(3-hydroxypropionate) block copolymer can be obtained at a high conversion rate and yield.

The polylactide-poly(3-hydroxypropionate) block copolymer prepared by the method according to the one embodiment can have a weight average molecular weight of 10,000 to 400,000, 15,000 to 350,000, 20,000 to 300,000, or 25,000 to 250,000.

As described above, in the preparation of a conventional polylactide-poly(3-hydroxypropionate) block copolymer, when using poly(3-hydroxypropionate) by chemical synthesis as an initiator, poly(3-hydroxypropionate) with various molecular weights can be used and thus, the structure and molecular weight of the polylactide-poly(3-hydroxypropionate) block copolymer can be adjusted, and the physical properties of the polylactide-poly(3-hydroxypropionate) block copolymer vary depending on the structure and molecular weight, so that the possibility of applying it to various fields can be confirmed. Since it exhibits excellent mechanical properties such as tensile strength and elongation at break while having excellent flexibility, the problem of brittleness of the conventional polylactide resin can be solved and its application field can be expanded.

EXAMPLES

Hereinafter, the present disclosure will be described in more detail with reference to examples. However, these examples are for illustrative purposes only, and the scope of the invention is not intended to be limited by these examples.

Examples 1 to 4

(1) Biosynthesis of Poly(3-Hydroxypropionate) Oligomer
1) Preparation of High Molecular Weight Poly(3-Hydroxypropionate)

For the biosynthesis of high molecular weight poly(3-hydroxypropionate) according to the present disclosure, first, fermentation was carried out based on the following conditions in order to prepare a fermentation broth containing 3-hydroxypropionate as a fermentation substrate. Specifically, $E.$ $coli$ W3110 having GDH and ALDH enzyme genes was used as a strain for fermentation. M9 was used as a medium, and 70 g/L of glycerol was used as a substrate and fermented to prepare 3-hydroxypropionate.

Thereafter, P (3HP) was fermented and produced using the 3-hydroxypropionate prepared above as a substrate. For fermentation, specifically a 5 L fermentation device (internal volume: 3 L) was used. RecC gene, a polyhydroxyalkanoate synthase (PHA synthase) derived from $Ralstonia$ $eutropha$, and variant 540 (CPPCT_540) gene of propionyl-CoA transferase derived from $Clostridium$ $propionicum$ were cloned into pBLuescript II KS+ vector, and the cloned recombinant vector was transformed into XL1-Blue $E.$ $coli$ to produce a recombinant $E.$ $coli$, which was used as the microorganism for fermentation.

The CPPCT_540 gene is an improved gene in which the base sequence is modified to express alanine instead of valine, the amino acid at position 194, (V194A), and includes three silent mutations (T669C, A1125G, T1158C) with only DNA base substitutions that do not result in an amino acid change (WO09/022797).

As a medium, 20 g/L of glucose was added to MR (Modified Riesenberg) medium, and 2.0 g/L of a fermentation broth containing 3HP produced above was added as a substrate. This was aerated and fermented under the conditions of 300 rpm and 1 vvm to finally produce high molecular weight P (3HP).

2) Preparation of Low Molecular Weight Poly(3-Hydroxypropionate)

In order to prepare low molecular weight poly(3-hydroxypropionate), in accordance with the method disclosed in Korean Unexamined Patent Publication No. 10-2017-0028186 (this document is incorporated by reference herein), a variant of propionyl-CoAtransferase (CP-PCT) derived from $Clostridium$ $propionicum$ was used as propionyl-CoA transferase gene (pct), a variant of PHA synthase derived from $Pseudomonas$ sp. MBEL 6-19 (KCTC 11027BP) as a PHA synthase gene, and pBluescript II (Stratagene Co., USA) as a vector to produce pPs619C1310-CPPCT540 recombinant vector. Using this, the pPs619C1249.18H-CPPCT540 vector was produced, and $E.$ $coli$ XL1-BlueAldhA in which ldhA was knocked out was transformed by electroporation to produce recombinant $E.$ $coli$ XL1-BlueΔldhA.

By using the recombinant $E.$ $coli$ XL1-BlueΔldhA prepared above, and a fermentation broth containing 3-hydroxypropionate prepared as a fermentation substrate by the same method as used in the preparation of the high molecular weight poly(hydroxypropionate), flask cultivation was performed to produce poly(3-hydroxypropionate). First, for seed culture, the recombinant $E.$ $coli$ was cultured in 3 mL of LB medium containing 100 mg/L ampicillin and 20 mg/L kanamycin [Bacto™ Triptone(BD) 10 g/L, Bacto™ yeast extract(BD) 5 g/L, NaCL(amresco) 10 g/L] for 12 hours. For this cultivation, 1 ml of the precultured solution was inoculated in 100 ml MR medium further containing fermentation broth containing 1 g/L of 3-hydroxypropionate and 100 mg/L of Ampicillin, 20 mg/L of Kanamycin and 10 mg/L Thiamine (per 1 L, Glucose 10 g, $KH_2PO_4$ 6.67 g, $(NH_4)_2HPO_4$ 4 g, $MgSO_4 \cdot 7H_2O$ 0.8 g, citric acid 0.8 g, and trace metal solution 5 mL; wherein trace metal solution is 5M HCl 5 mL, $FeSO_4 7H_2O$ 10 g, $CaCl_2$ 2 g, $ZnSO_4H_2O$ 2.2 g, $MnSO_4 \cdot 4H_2O$ 0.5 g, $CuSO_4 \cdot 5H_2O$ 1 g, $(NH_4)6Mo_7O_2 \cdot 4H_2O$ 0.1 g, and $Na_2B_4O_2 \cdot 10H_2O$ 0.02 g, per 1 L) and cultured at 30° C. for 3 days while stirring at 250 rpm.

The culture solution was centrifuged at 4° C. and 4000 rpm for 10 minutes to recover the cells, washed twice with a sufficient amount of distilled water, and dried at 80° C. for 12 hours to finally prepare P (3HP) having a molecular weight of 10,200.

3) Preparation of Poly(3-Hydroxypropionate) Oligomers Having Various Weight Average Molecular Weights High molecular weight poly(hydroxypropionate) having a weight average molecular weight of 20,000 g/mol prepared in 1) was placed in distilled water, and hydrolyzed under acid catalyst conditions by adjusting the pH to 2 using hydrochloric acid. To accelerate the hydrolysis, a poly (hydroxypropionate) sample was hydrolyzed in an oven at 100° C. for 24 hours and 72 hours, respectively, and poly (3-hydroxypropionate) oligomers each having a weight average molecular weights of 2100 and 21800 (g/mol) was obtained.

(2) Preparation of Polylactide-Poly(3-Hydroxypropionate) Block Copolymer

In a 500 mL round flask, 16 g of L-lactide, poly(3-hydroxypropionate) oligomer having various weight average molecular weights prepared in (1) and 0.04 g of tin (II) 2-ethylhexanoate (0.1 mol %; Sigma Aldrich) were added in the amount shown in Table 1 below, and vacuum-dried at room temperature for 4 hours by applying sufficient vacuum.

Thereafter, the flask was placed in an oil bath pre-heated at 130° C., and heated to 180° C., and then subjected to a ring-opening polymerization reaction for 20 minutes. After completion of the reaction, the reaction product was dissolved in chloroform and extracted with methanol to recover the block copolymer.

TABLE 1

| (unit: g) | Molecular weight of poly(3-hydroxypropionate) [Mw, g/mol] | Content of poly(3-hydroxypropionate) (Compared to lactide) | |
|---|---|---|---|
| | | [wt %] | [mol %] |
| Example 1 | 2100 | 10 | 0.34 |
| Example 2 | 10200 | 10 | 0.07 |
| Example 3 | 21800 | 10 | 0.06 |
| Example 4 | 21800 | 5 | 0.03 |

Comparative Examples 1 and 2

In a 500 mL round flask, L-lactide, dodecanol, and tin(II) 2-ethylhexanoate were added in the amounts shown in Table 2 below, and vacuum-dried at room temperature for 4 hours by applying sufficient vacuum.

Thereafter, the flask was placed in an oil bath pre-heated at 130° C., and heated to 180° C., and then subjected to a ring-opening polymerization reaction for 20 minutes. After completion of the reaction, the reaction product was dissolved in chloroform and extracted with methanol to recover the copolymer.

TABLE 2

| (unit: g) | L-lactide | Tin(II) 2-ethylhexanoate | Dodecanol |
|---|---|---|---|
| Comparative Example 1 | 16.00 | 0.04 (0.1 mol % relative to lactide) | 0.16 (0.1 mol % relative to lactide) |
| Comparative Example 2 | 16.00 | 0.04 (0.1 mol % relative to lactide) | 0.80 (0.1 mol % relative to lactide) |

Evaluation

1. NMR(Nuclear Magnetic Resonance) Analysis

NMR analysis was performed at room temperature using an NMR spectrometer including a Varian Unity Inova (500 MHz) spectrometer having 5 mm triple resonance probe. The block copolymers and polymers each prepared in Examples 1 to 4 as the analytes were diluted in a solvent for NMR measurement ($CDCl_3$) to a concentration of about 10 mg/ml and used. Chemical shifts are expressed in ppm.

FIG. 1 is a graph showing the results of NMR analysis of block copolymers produced in Examples 1 to 4. According to FIG. 1, in the NMR analysis graph of the block copolymers of Examples 1 to 4 according to the present disclosure, both a polylactide peak and a poly(3-hydroxypropionate) peak were observed.

In addition, as a result of the NMR analysis of Examples 1 to 4, the integral ratio of the poly(3-hydroxypropionate) peak was calculated from the graph, which is shown in Table 3.

TABLE 3

| Sample | Amount of poly(3-hydroxypropionate) actually added (wt %) | NMR analysis (wt %) |
|---|---|---|
| Example 1 | 10.0% | 17.0% |
| Example 2 | 10.0% | 12.0% |
| Example 3 | 10.0% | 12.0% |
| Example 4 | 5.0% | 7.0% |

According to FIG. 1, since the "content of poly(3-hydroxypropionate) in NMR analysis" is similar to "the amount of poly(3-hydroxypropionate) actually added", it can be predicted that the poly(3-hydroxypropionate) oligomer used in the method for preparing the block copolymer of Examples 1 to 4 was mostly used as a reactant.

2. GPC (Gel Permeation Chromatography) Analysis

The weight average molecular weight (Mw) and the number average molecular weight (Mn) of the block copolymers of Examples 1 to 4 and the polymers of Comparative Examples 1 and 2 were each determined by gel permeation chromatography (GPC) (Waters: Waters707). The block copolymer/polymer to be measured was dissolved in tetrahydrofuran so as to have a concentration of 4000 ppm, and 100 μl was injected into the GPC. Tetrahydrofuran was used as the mobile phase of the GPC and inflowed at a flow rate of 1.0 mL/min, and the analysis was performed at 35° C. The column consisted of four Waters HR-05,1,2,4E connected in series. RI and PAD Detector was used as the detector, and the measurement was performed at 35° C. The results are shown in Table 4 below.

TABLE 4

| | Content of initiator actually used (mol %) | Number average molecular weight (Mn) | Weight average molecular weight (Mw) | Polydispersity index (PDI) |
|---|---|---|---|---|
| Comparative Example 1 | 0.1 | 55,984 | 115,050 | 2.06 |
| Comparative Example 2 | 0.05 | 91,731 | 180,524 | 1.97 |
| Example 1 | 0.34 | 17,400 | 22,700 | 1.31 |
| Example 2 | 0.07 | 43,600 | 67,300 | 1.13 |
| Example 3 | 0.06 | 53,100 | 83,800 | 1.58 |
| Example 4 | 0.03 | 68,700 | 120,000 | 1.74 |

Polydispersity Index (PDI): Calculated by dividing the measured weight average molecular weight by the number average molecular weight.

According to Table 4, when dodecanol was used as an initiator as in Comparative Examples 1 and 2, it was confirmed that the number average molecular weight and the weight average molecular weight of the polymer decreased as the content of dodecanol increased. Similarly, in the case of the polylactide-poly (3-hydroxypropionate) block copolymer prepared in Examples 1 to 4, it was confirmed that the molecular weight was larger than that of poly(3-hydroxypropionate) oligomer. In addition, as the content of the poly(3-hydroxypropionate) added increases, the number average molecular weight and the weight average molecular weight of the block copolymer decrease, confirming that poly(3-hydroxypropionate) acts as an initiator.

The invention claimed is:

1. A method for preparing a block copolymer comprising the steps of:
    (a) biosynthesizing a poly (3-hydroxypropionate) initiator; and
    (b) subjecting a lactide monomer to a ring-opening polymerization in the presence of the poly (3-hydroxypropionate) initiator prepared in step (a) to prepare a polylactide-poly (3-hydroxypropionate) block copolymer, wherein the ring-opening polymerization is performed at a temperature of 150° C. to 180° C. for 5 minutes to 20 minutes;
    wherein the method further comprises a step of hydrolyzing the poly (3-hydroxypropionate) initiator prepared in the step (a), before performing the step (b), wherein the hydrolysis is performed for 4 to 80 hours at room temperature to 200° C.,
    wherein the poly (3-hydroxypropionate) initiator has a weight average molecular weight of 1,500 to 200,000 g/mol.

2. The method for preparing a block copolymer according to claim 1, wherein the step (a) is performed by a recombinant microorganism expressing one or more enzymes capable of providing hydroxyacyl-CoA and/or a PHA synthase.

3. The method for preparing a block copolymer according to claim 1, wherein a hydrolyzing agent used in the hydrolysis is an acid hydrolyzing agent, a base hydrolyzing agent, a PHA depolymerase, or a combination thereof.

4. The method for preparing a block copolymer according to claim 1, wherein an amount of the poly (3-hydroxypropionate) initiator is 0.01 parts by weight or more based on 100 parts by weight of the lactide monomer.

5. The method for preparing a block copolymer according to claim 1, wherein the ring-opening polymerization is performed under one or more catalysts selected from the group consisting of an organic metal complex catalyst and an organic catalyst.

6. The method for preparing a block copolymer according to claim 5, wherein the organic metal complex catalyst is a catalyst of Chemical Formula 1:

$$MA^1_p A^2_{2-p} \qquad \text{<Chemical Formula 1>}$$

wherein in Chemical Formula 1, M is Al, Mg, Zn, Ca, Sn, Fe, Y, Sm, Lu, Ti or Zr, p is an integer of 0 to 2, and $A^1$ and $A^2$ are each independently an alkoxy or carboxyl group.

7. The method for preparing a block copolymer according to claim 6, wherein the $MA^1_p A^2_{2-p}$ is tin (II) 2-ethylhexanoate $(Sn(Oct)_2)$.

8. The method for preparing a block copolymer according to claim 5, wherein an amount of the catalyst is 0.01 to 10 mol % based on the mole amount of the lactide monomer.

9. The method for preparing a block copolymer according to claim 1, wherein the ring-opening polymerization is performed by bulk polymerization.

10. The method for preparing a block copolymer according to claim 1, wherein the polylactide-poly (3-hydroxypropionate) block copolymer has a weight average molecular weight of 10,000 to 400,000 g/mol.

\* \* \* \* \*